(12) United States Patent
Dooney, Jr. et al.

(10) Patent No.: US 11,771,416 B2
(45) Date of Patent: Oct. 3, 2023

(54) SURGICAL TOOLS AND ASSOCIATED GRAFT AUGMENTATION TECHNIQUES

(71) Applicant: ARTHREX, INC., Naples, FL (US)

(72) Inventors: Thomas Dooney, Jr., Naples, FL (US); Orr Limpisvasti, Manhattan Beach, CA (US)

(73) Assignee: Arthrex, Inc., Naples, FL (US)

( * ) Notice: Subject to any disclaimer, the term of this patent is extended or adjusted under 35 U.S.C. 154(b) by 459 days.

(21) Appl. No.: 16/928,479

(22) Filed: Jul. 14, 2020

(65) Prior Publication Data
US 2022/0015756 A1    Jan. 20, 2022

(51) Int. Cl.
*A61B 7/04* (2006.01)
*A61B 17/04* (2006.01)

(52) U.S. Cl.
CPC ...... *A61B 17/0469* (2013.01); *A61B 17/0401* (2013.01); *A61B 2017/0409* (2013.01); *A61B 2017/0464* (2013.01); *A61B 2017/0479* (2013.01)

(58) Field of Classification Search
CPC ........ A61B 17/0469; A61B 2017/0409; A61B 2017/0464
See application file for complete search history.

(56) References Cited

U.S. PATENT DOCUMENTS

| | | | |
|---|---|---|---|
| 5,405,360 A * | 4/1995 | Tovey | A61F 2/0063 606/151 |
| 5,423,857 A * | 6/1995 | Rosenman | A61B 17/10 606/151 |
| 5,497,933 A * | 3/1996 | DeFonzo | A61B 17/0684 227/176.1 |
| 5,695,525 A * | 12/1997 | Mulhauser | A61F 2/02 606/151 |
| 5,797,929 A * | 8/1998 | Andreas | A61B 17/0469 606/139 |
| 6,723,041 B2 | 4/2004 | Lau et al. | |
| 7,326,222 B2 * | 2/2008 | Dreyfuss | A61B 17/0483 606/103 |
| 8,585,773 B1 | 11/2013 | Kucklick | |
| 8,864,780 B2 | 10/2014 | Euteneuer et al. | |
| 9,005,224 B2 | 4/2015 | Euteneuer et al. | |
| 9,101,460 B2 | 8/2015 | Euteneuer et al. | |
| 9,113,977 B2 | 8/2015 | Euteneuer et al. | |
| 9,179,910 B2 | 11/2015 | Euteneuer et al. | |
| 9,179,961 B2 | 11/2015 | Euteneuer et al. | |
| 9,198,751 B2 | 12/2015 | Euteneuer et al. | |
| 9,314,331 B2 | 4/2016 | Euteneuer et al. | |
| 2003/0069467 A1 | 4/2003 | Lau et al. | |
| 2005/0065535 A1 * | 3/2005 | Morris | A61B 17/0469 606/148 |
| 2006/0009802 A1 | 1/2006 | Modesitt | |

(Continued)

*Primary Examiner* — Alexander J Orkin

(74) *Attorney, Agent, or Firm* — Carlson, Gaskey & Olds, P.C.

(57) ABSTRACT

This disclosure relates to surgical tools and methods. The surgical tools can include a handle, which includes an outer surface. A first rod extends from the handle and includes a first lumen. A second rod extends from the handle and includes a second lumen. A first set of suture cleating channels are formed in the outer surface. A second set of suture cleating channels are formed in the outer surface and spaced apart from the first set of suture cleating channels.

8 Claims, 11 Drawing Sheets

(56) References Cited

U.S. PATENT DOCUMENTS

| | | |
|---|---|---|
| 2009/0156986 A1 | 6/2009 | Trenhaile |
| 2009/0156997 A1* | 6/2009 | Trenhaile .............. A61F 2/0063 604/99.01 |
| 2010/0069930 A1* | 3/2010 | Roslin ................ A61B 17/0057 606/151 |
| 2011/0040311 A1 | 2/2011 | Levin et al. |
| 2012/0209401 A1 | 8/2012 | Euteneuer et al. |
| 2014/0107675 A1* | 4/2014 | Hansen ................ A61F 2/0063 606/151 |
| 2014/0172016 A1* | 6/2014 | Housman ........... A61B 17/0401 606/232 |
| 2016/0157980 A1* | 6/2016 | Poucher ........... A61B 17/06166 600/30 |
| 2017/0000476 A1* | 1/2017 | Dougherty ......... A61B 17/0469 |
| 2017/0095324 A1* | 4/2017 | Adams ...................... A61F 2/08 |
| 2017/0172562 A1* | 6/2017 | Lombardo ......... A61B 17/0401 |
| 2019/0336261 A1* | 11/2019 | Ravenscroft ..... A61B 17/06166 |

\* cited by examiner

SURGICAL TOOLS AND ASSOCIATED GRAFT AUGMENTATION TECHNIQUES

BACKGROUND

This disclosure relates to surgical tools and assorted surgical techniques for graft augmentation.

Normal joint kinematics are achieved through balanced soft tissues that surround the articulating bones of a joint. An unstable joint can occur if there is significant disruption of the articulating bones or the surrounding soft tissues. Unstable joints can also occur within a replaced joint subsequent to an arthroplasty procedure. The resulting joint instability may cause pain, dysfunction, accelerated bone loss, soft tissue tears and premature arthritis.

SUMMARY

This disclosure relates to surgical tools and techniques. Surgical tools may include a handle and one or more rods extending from the handle. The surgical tools may be positionable between a folded position and a spread position. The techniques may be employed for graft augmentation.

A surgical tool assembly according to an exemplary aspect of this disclosure may include, inter alia, a handle including an outer surface. A first rod extends from the handle and includes a first lumen. A second rod extends from the handle and includes a second lumen. A first set of suture cleating channels are formed in the outer surface. A second set of suture cleating channels are formed in the outer surface and spaced apart from the first set of suture cleating channels.

A method according to an exemplary aspect of this disclosure may include, inter alia, passing a suture through a graft, routing the suture through a first lumen of a first arm of a surgical tool, cleating the suture within a channel formed in an outer surface of a handle of the surgical tool, folding the graft on the surgical tool, inserting the folded graft through a cannula or an open incision, unfolding the graft over a soft tissue, and securing the graft to the soft tissue with at least one fastener.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

Figure 1:
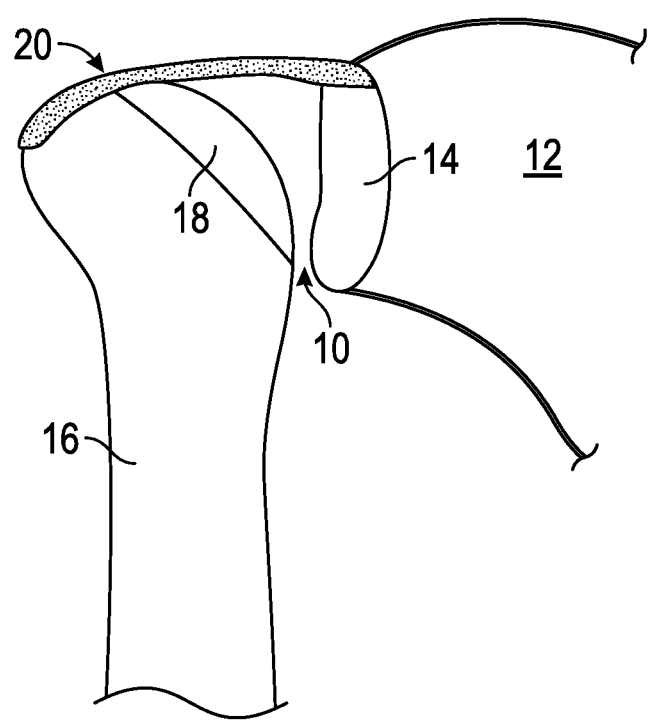
FIG. 1 illustrates a joint of a human musculoskeletal system.

FIG. 1 illustrates a joint 10 of the human musculoskeletal system. The joint 10 may be any joint of the musculoskeletal system of the human body. In an embodiment, the joint 10 is the glenohumeral joint of a shoulder. The joint 10 includes multiple bones including a scapula 12 and a humerus 16. Some of these bones articulate relative to one another. For example, the joint 10 includes a ball and socket joint formed between a head 18 of the humerus 16 and a glenoid 14, which is a cup-like recession of the scapula 12 configured to receive the head 18.

A capsule 20 generally covers the joint 10 and is surrounded and reinforced by various muscles, tendons and ligaments that are responsible for keeping the adjoining bones of the joint 10 together. The joint 10 may become unstable if there is significant disruption of the articulating bones (e.g., the humerus 16 and the glenoid 14), the capsule 20, or other surrounding muscles, tendons and/or ligaments. In an embodiment, the joint 10 could become unstable in response to a massive irreparable rotator cuff tear.

This disclosure describes graft augmentation techniques for repairing or reconstructing an unstable joint, such as in response to a massive irreparable rotator cuff tear or other injury. Although graft augmentation techniques associated with a shoulder joint are described throughout this disclosure as embodiments, this disclosure is not intended to be limited to shoulder surgeries. In other words, the various techniques described herein may be employed to reconstruct and/or improve the functionality of any joint of the human musculoskeletal system.

Figure 2:
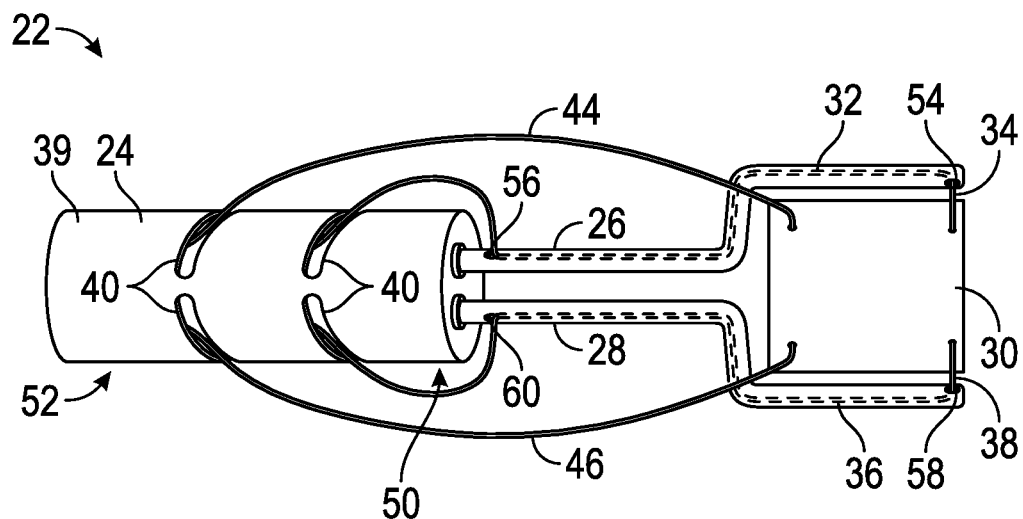
FIG. 2 illustrates an exemplary surgical tool.

FIG. 2 illustrates an exemplary surgical tool 22 that may be used in a surgical procedure, such as a graft augmentation technique, for example. The surgical tool 22 includes a handle 24, and a first rod 26 and a second rod 28 extending from the handle 24. The surgical tool 22 is configured to hold a graft 30 and may be utilized for shuttling the graft 30 to a graft site, such as within a joint space as shown in FIG. 1, for example. The first rod 26 defines a first lumen 32 that may receive a first suture 34 extending from the graft 30. The second rod 28 defines a second lumen 36 that may receive a second suture 38 extending from the graft 30.

The handle 24 includes an outer surface 39. A first set of channels 40 and a second set of channels 42 may be formed in the outer surface 39. In an embodiment, the first and second sets of channels 40, 42 are configured as notches formed in the outer surface 39. The first and second sutures 34, 38 may be received in the first set of channels 40. Third and fourth sutures 44, 46 may extend from the graft 30 to the second set of channels 42. In some embodiments, as shown, the handle 24 includes a distal end 50 and a proximal end 52, the rods 26, 28 extend from the distal end, and the first set of channels 40 are nearer the distal end 50 than the second set of channels 42. In some embodiments, the first set of channels 40 may include two channels that are angled to converge toward one another as they extend proximally to distally. The second set of channels 42 may be similarly angled and may also include two channels. As described herein, the sutures 34, 38, 44, 46 can be cleated within the sets of channels 40,42 to hold a position of the graft 30. In some embodiments, the angling of the channels 40, 42 aids in cleating the sutures 34, 38, 44, 46.

The first lumen 32 may extend over at least a portion of an interior length of the first rod 26, and the second lumen 36 may extend over at least a portion of an interior length of the second rod 28. In an embodiment, the first lumen 32 extends at least from a first opening 54 near a distal end of the first rod 26 to a second opening 56 near a proximal end of the first rod 26, such that the first suture 34 may be routed from the graft 30, through the distal opening 54, through the first lumen 32, through the proximal opening 56, and then into one of the first set of channels 40. The second lumen 36 may have similarly configured openings 58, 60 for routing the second suture 38 through the second rod 28. Although the first and second sutures 34, 38 are shown with one end routed through the lumens 32, 36 in the illustration in FIG. 2, two ends may be routed through the lumens 32, 36 and to the first set of channels 40 in some embodiments. In addition, although each is shown as accommodating a single suture, additional sutures could optionally be passed through the lumens 32, 36.

In some embodiments, one or both of the first rod 26 and the second rod 28 is movable between a folded position and a spread position. FIG. 2 illustrates an exemplary spread position of the rods 26, 28 of the surgical tool 22. In some embodiments, pulling free ends of the third and fourth sutures 44, 46 to be tensioned maintains the graft 30 in the spread position. In some embodiments, the spread position of the graft 30 mimics the desired implanted position of the graft 30 during a procedure.

In some embodiments, the graft 30 may include either an allograft or an autograft. In some embodiments, the graft 30 is an acellular dermal extracellular matrix. ArthroFlex®, sold by Arthrex, Inc., is one type of graft 30 suitable for use to perform an exemplary graft augmentation technique. In some embodiments, the graft 30 may be a suture patch or any other synthetic augmentation. The sutures 34, 38, 44, 46 may include suture strands, suture tape, any other suture-like product, or any thread-like material, which may be attached to a graft 30. Moreover, although four sutures are shown attached to the graft 30 in FIG. 2, the total number of sutures passed through the graft 30 could vary and is not intended to limit this disclosure. The surgical tool 22, the graft 30, and the sutures 34, 38, 44, 46 may form a surgical tool assembly.

Figure 3:
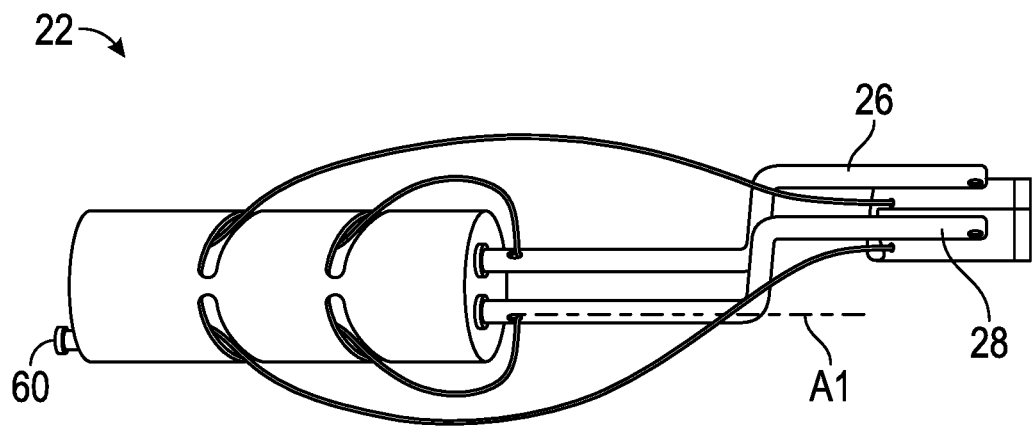
FIG. 3 illustrates the exemplary surgical tool of FIG. 2 in a folded position.

FIG. 3 illustrates an exemplary folded position of the rods 26, 28 of the exemplary surgical tool 22. The first rod 26 and the second rod 28 are closer together in the folded position than in the spread position. In some embodiments, as shown, the second rod 28 is rotatable about an axis A1 between the folded position and the spread position, and the first rod 26 is fixed against movement or rotation. In some embodiments, both rods 26, 28 are rotatable. Other movements, including non-rotational movements, between folded and spread positions may also be utilized in some embodiments. In some embodiments, the surgical tool 22 may be moved to the folded position to fold the graft 30 for ease of insertion through an opening, one embodiment being an arthroscopic portal, such as a cannula, during an arthroscopic procedure. In some embodiments, the surgical tool 22 may include a knob 60 for rotational input to the second rod 28. In other embodiments, such as shown in FIGS. 7-12B, a switch (see feature '272') may be utilized to move between the folded and spread positions.

Figure 4:
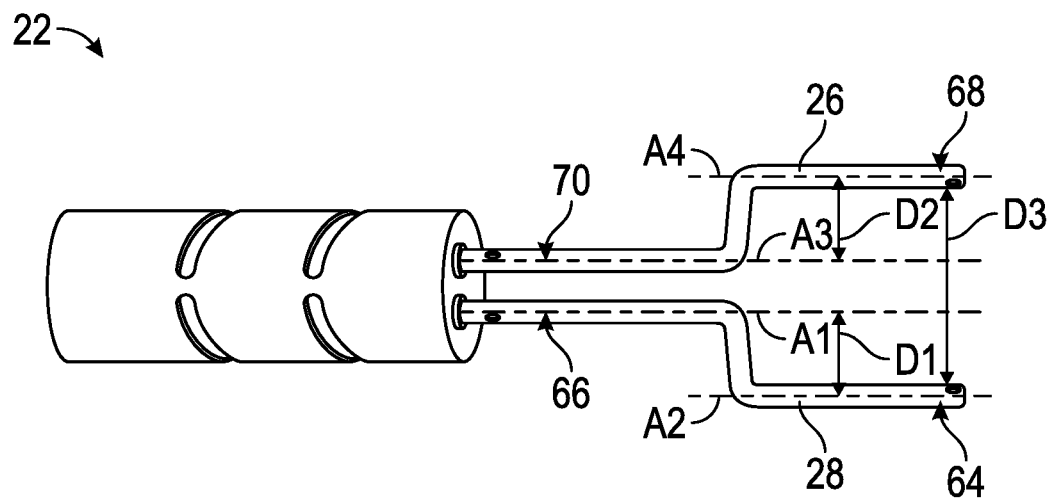
FIG. 4 illustrates the exemplary surgical tool of FIGS. 2-3.

As shown in FIG. 4, one or both of the rods 26, 28 may include offset configurations. In the embodiment shown, both rods 26, 28 have offset configurations. The second rod 28 includes an offset portion 64 that is offset from a main portion 66, such that a central axis A2 extending through the offset portion 64 is spaced a distance D1 from the axis A1. The first rod 26 may include an offset portion 68 that is offset from a main portion 70, such that a central axis A4 extending through the offset portion 68 is spaced a distance D2 from a central axis A3 through the main portion 70. In some embodiments, the axes A1, A2, A3, A4 are about parallel. In this disclosure, the term "about" means that the expressed quantities or ranges need not be exact but may be approximated and/or larger or smaller, reflecting acceptable tolerances, conversion factors, measurement error, etc.

In the embodiment shown, in the spread position, the offset portion 64 of the second rod 28 is its greatest distance D3 from the offset portion 68 of the first rod 26, such that the coverage of the graft 30 is maximized in the spread position. Utilizing one or more offsets allows the distance D3 to be greater than it would be without offsets, thus providing greater control and stability when shuttling and placing the graft 30 (see FIGS. 2 and 3) during a graft augmentation procedure.

Figure 5:
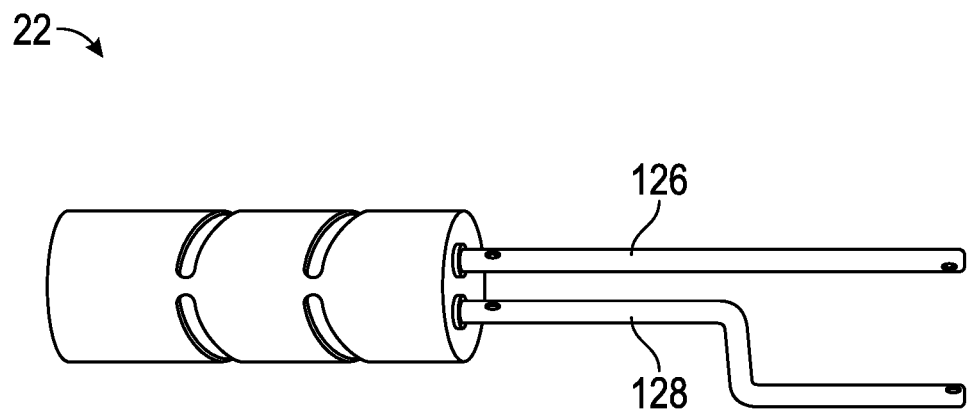
FIG. 5 illustrates another exemplary surgical tool.

FIG. 5 illustrates another exemplary surgical tool 122 having a first rod 126 in a non-offset configuration and a second rod 128 in an offset configuration. It should be understood that like reference numerals identify corresponding or similar elements throughout the several drawings. It should also be understood that although particular component arrangements are disclosed and illustrated in these embodiments, other arrangements could also benefit from the teachings of this disclosure. In this embodiment, the first rod 126 may be fixed against rotation and/or movement, while the second rod 128 may be configured to rotate between a folded and spread position.

FIGS. 6-13D schematically illustrate, in sequential order, an exemplary graft augmentation technique 200. Fewer or additional steps than are recited below could be performed within the scope of this disclosure. In addition, the recited order of steps shown in FIGS. 6-13D is not intended to limit this disclosure.

Figure 6:
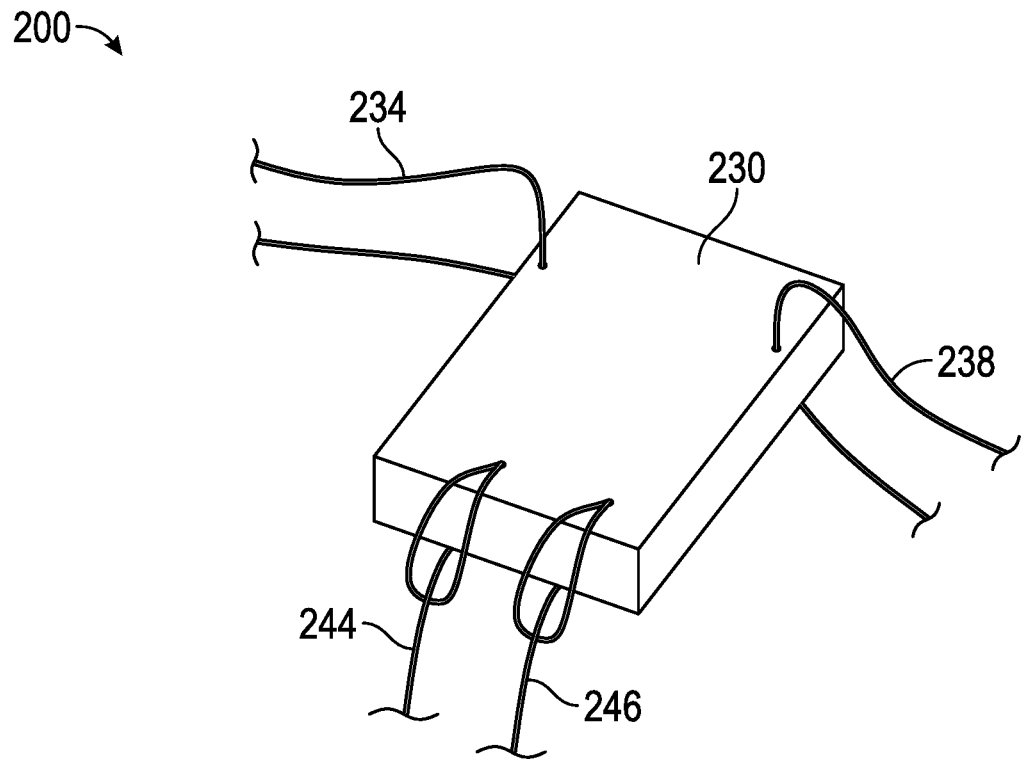
FIG. 6 schematically illustrates the passage of sutures through a graft as part of an exemplary graft augmentation technique.

Referring first to FIG. 6, a surgeon may begin the exemplary graft augmentation technique 200 by preparing a graft 230 and passing a plurality of sutures 234, 238, 244, 246 through the graft 230. In some embodiments, as shown, the sutures 234, 238 are attached to the graft 230 with a U-shaped attachment, such that each suture 234, 238 passes through the graft 230 and provides two free ends, and pulling on one free end can remove the suture 234, 238 from the graft 230, as discussed further below. The exemplary sutures 244, 246 may be attached with a luggage tag style attachment. Other suture attachment styles are contemplated for other embodiments. In some embodiments, as shown, the sutures 234, 238 are attached to a distal side of the graft 230, which may be a medial side relative to the desired implant position for a given anatomy, while the sutures 244, 246 are attached to a proximal side of the graft, which may be a lateral side relative to the desired implant position. In some embodiments, the graft 230 may be about 25 mm×30 mm in dimension. However, the actual size of the graft 230 is not intended to limit this disclosure.

Figure 7:
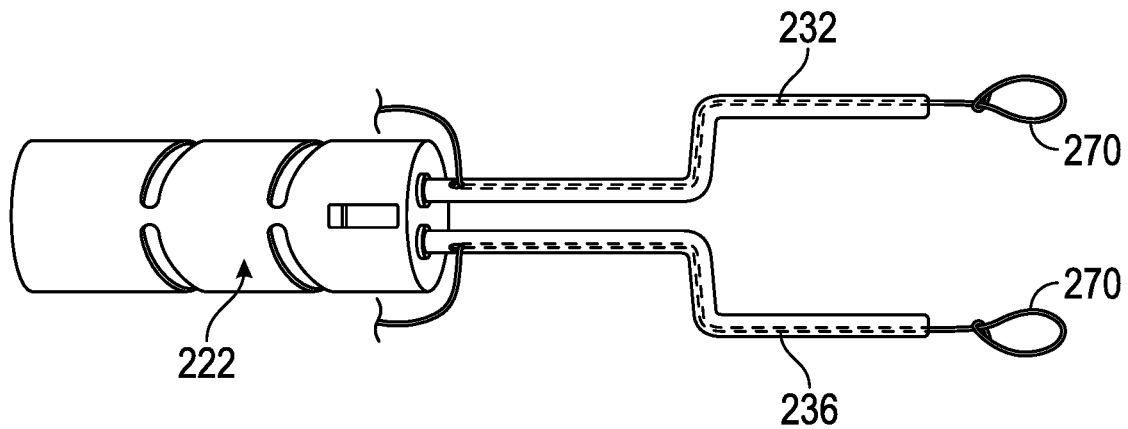
FIG. 7 illustrates another exemplary surgical tool.
Figure 8:
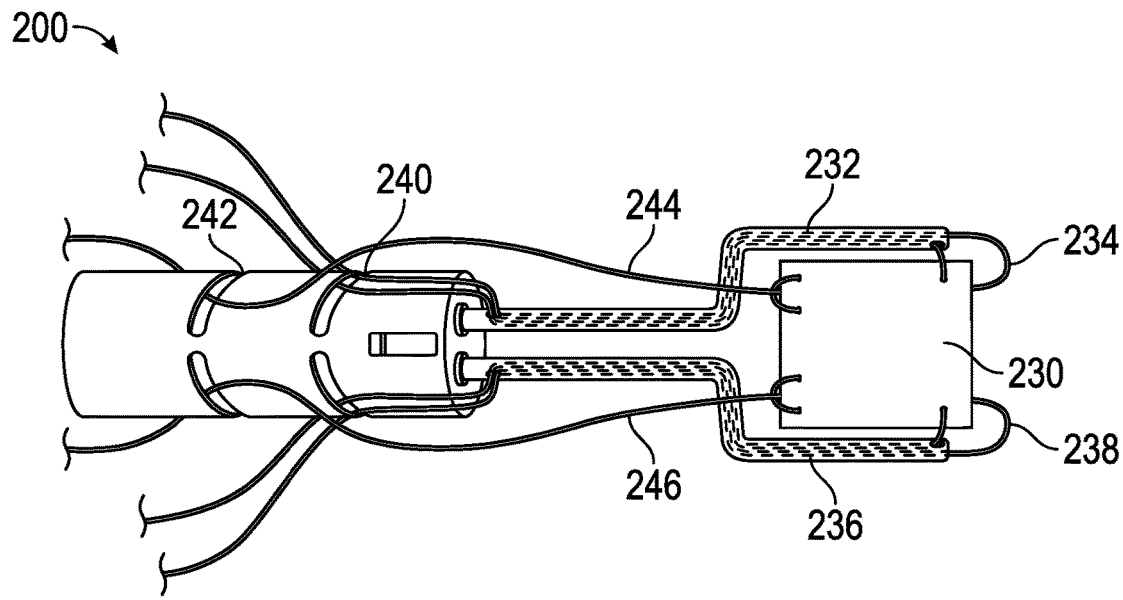
FIG. 8 illustrates the surgical tool and graft of FIGS. 6-7.

Next, as illustrated in FIGS. 7-8, loading loop sutures 270 provided within the lumens 232, 236 of the surgical tool 222 may be utilized to pull the sutures 234, 238 (see FIG. 6) through the lumens 232, 236. As shown in FIG. 8, the sutures 234, 238 may be passed through the lumens 232, 236, tensioned, and then cleated into the first set of channels 240. The sutures 244, 246 are utilized to tension the graft 230 and are then cleated into the second set of channels 242 without being passed through the lumens 232, 236.

Figure 9:
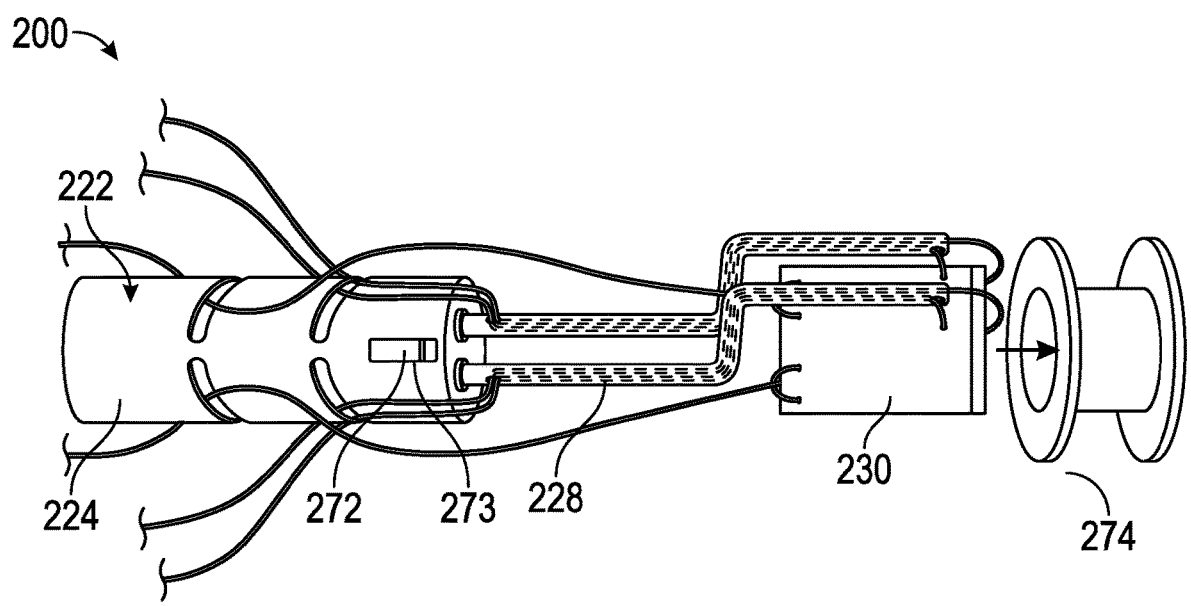
FIG. 9 schematically illustrates the surgical tool and graft of FIGS. 6-8 moved to the folded position and introduced through a portal during an exemplary graft augmentation technique.

Referring now to FIG. 9, the graft 230 may next be folded by moving the surgical tool 222 to the folded position as shown. In some embodiments, as shown, this may be done by moving a switch 272 on the handle 224 to rotate the rod 228 to the folded position. For example, the switch 272 may be moved proximally to distally within a slot 273. The folded graft 230 may then be inserted through a cannula 274 or other portal, as shown, or through an open incision in some embodiments.

Figure 10:
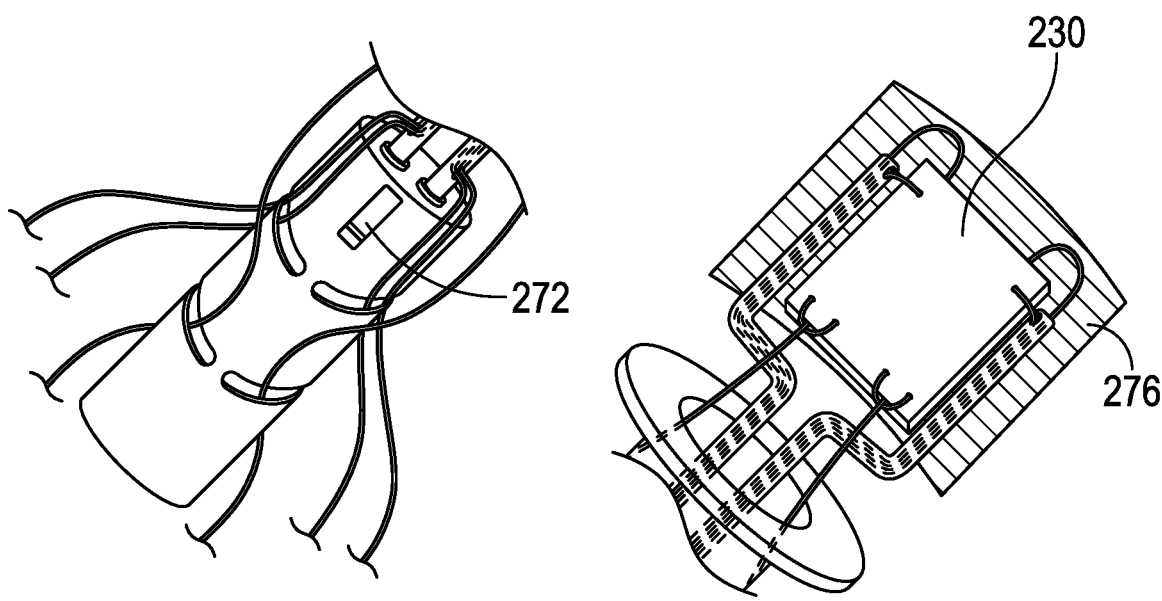
FIG. 10 schematically illustrates the surgical tool and graft of FIGS. 6-9 within a joint space.

As illustrated in FIG. 10, once the graft 230 is positioned over soft tissue 276, the graft 230 may be unfolded by moving the surgical tool 222 to the spread position. In some embodiments, the graft 230 is unfolded by moving the switch 272 in a distal to proximal direction within the slot 273. The surgical tool 222 holds the graft 230 open over the soft tissue 276 for fixation. The tissue 276 may be associated with a joint space, such as that shown in FIG. 1 in some embodiments.

Figure 11:
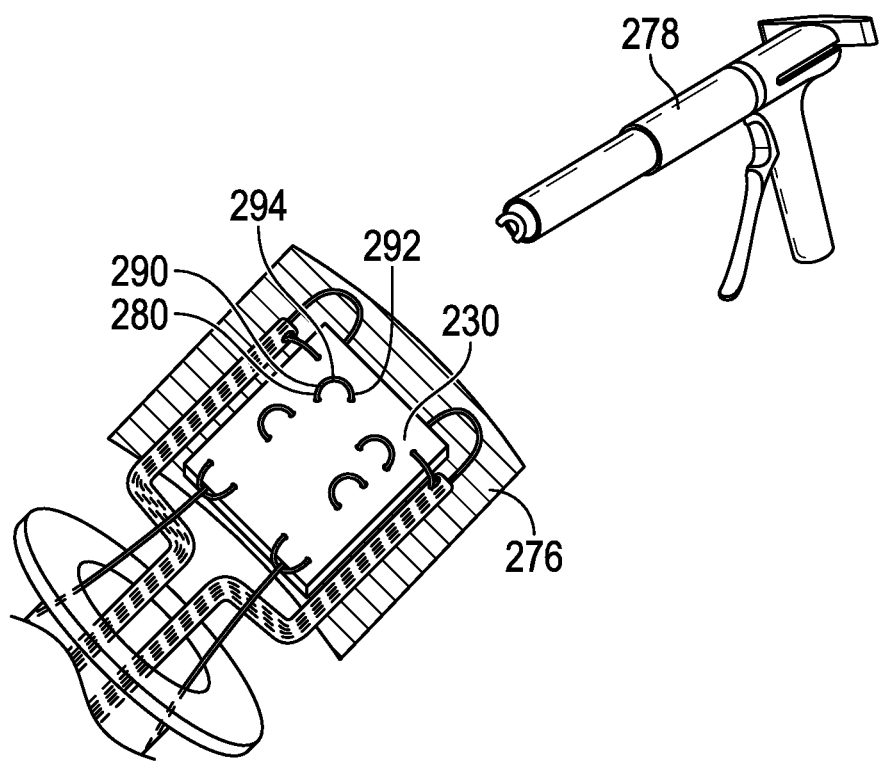
FIG. 11 schematically illustrates the fastening of the graft of FIGS. 6-10 to tissue during an exemplary graft augmentation technique.

Next, as illustrated in FIG. 11, with the graft 230 open over the soft tissue 276, a fastener delivery device 278 may be used to insert one or more fasteners 280 through the graft 230 into the soft tissue 276. In some embodiments, multiple fasteners 280 may be used if needed to secure the graft 230 to the soft tissue 276. The fastener may include first and second barbs 290, 292 connected by a bridge 294. The barbs 290, 292 pierce through tissue 276 and the bridge 294 rests over the graft 230 to secure it in place.

Figure 12A:
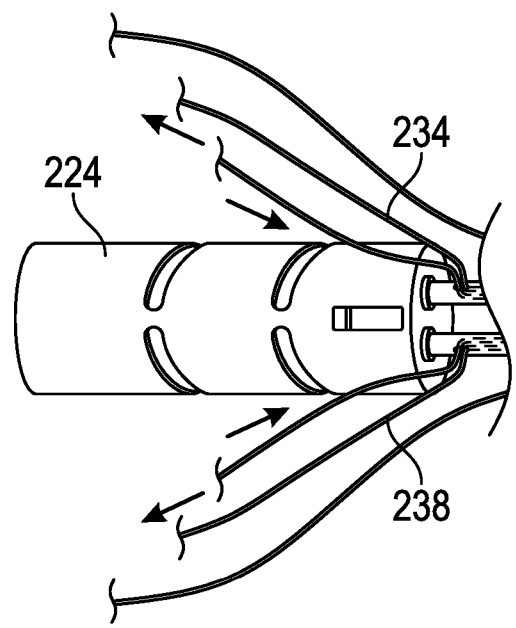
FIG. 12A schematically illustrates the uncleating and removal of sutures from the surgical tool of FIGS. 7-11 during an exemplary graft augmentation technique.
Figure 12B:
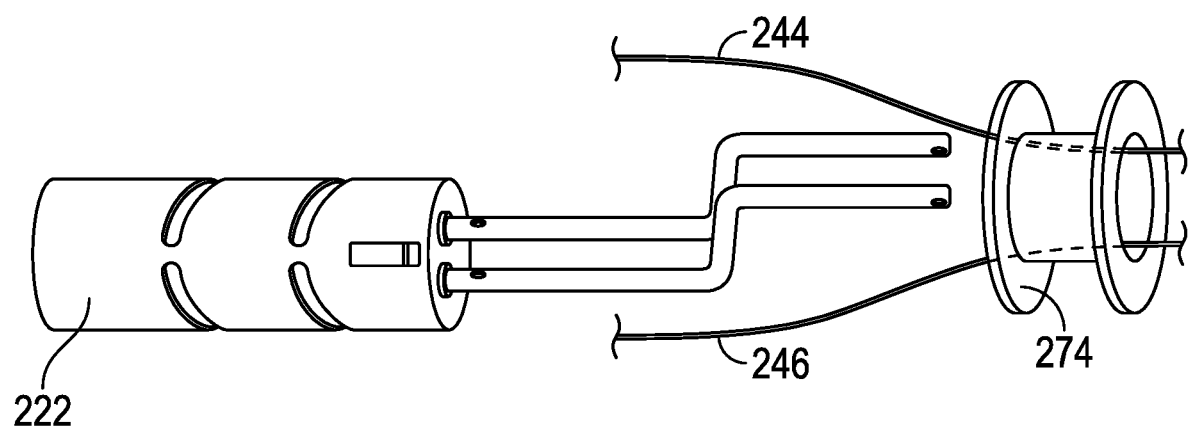
FIG. 12B schematically illustrates the removal of the surgical tool of FIGS. 7-12A from the joint space during an exemplary graft augmentation technique.

As illustrated in FIGS. 12A-12B, once the graft 230 is secured on the soft tissue 276, the surgical tool 222 may be prepared to be removed from the joint space. As shown in FIG. 12A, for example, the sutures 234, 238 may be uncleated from the handle 224. The surgeon may then pull on one free end of each of the sutures 234, 238 to remove the sutures 234, 238 from the graft 230 (not shown). As shown in FIG. 12B, the surgical tool 222 may then be moved to the folded position and removed from the joint space, such as through the cannula 274. As shown, the sutures 244, 246 may still be attached to the graft 230 and may be utilized for subsequent fixation to bone in some embodiments.

Figure 13A:
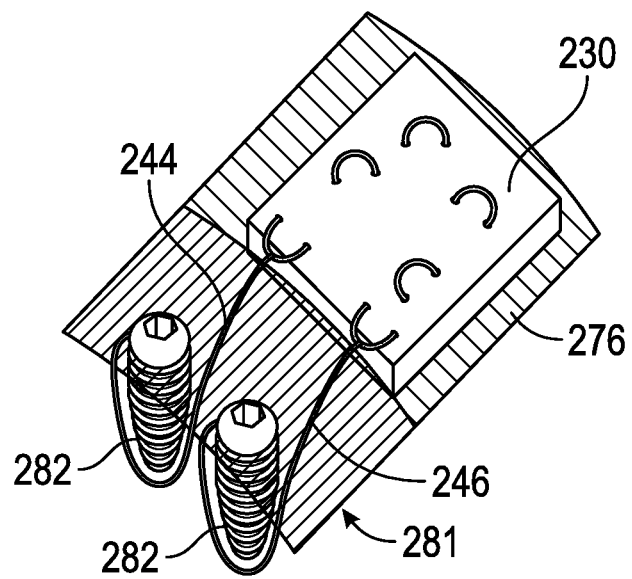
FIG. 13A schematically illustrates one exemplary method of fixation of a graft to bone.
Figure 13B:
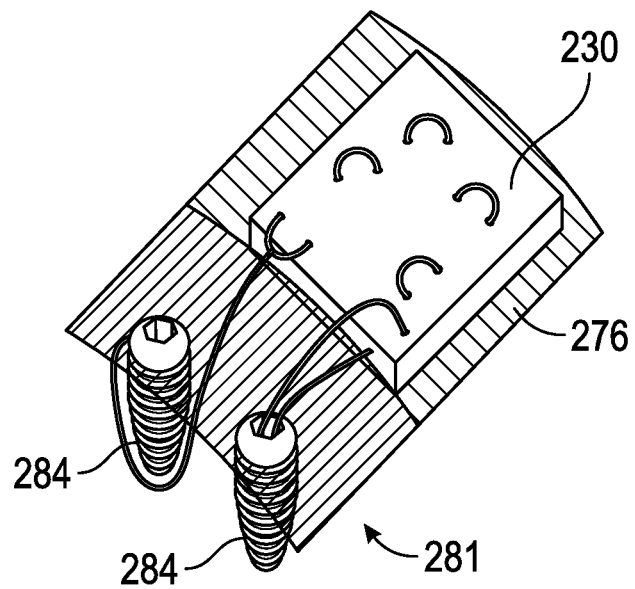
FIG. 13B schematically illustrates another exemplary method of fixation of a graft to bone.

For example, as illustrated in FIG. 13A, the graft 230 can be secured to bone 281 with the remaining sutures 244, 246, such as with standard knotless suture anchors 282. In alternative embodiments, as shown in FIG. 13B the sutures 244, 246, can be removed from the lateral side of the graft 230 and knot tying anchors 284 can be placed to secure the graft 230 to the bone 281.

Figure 13C:
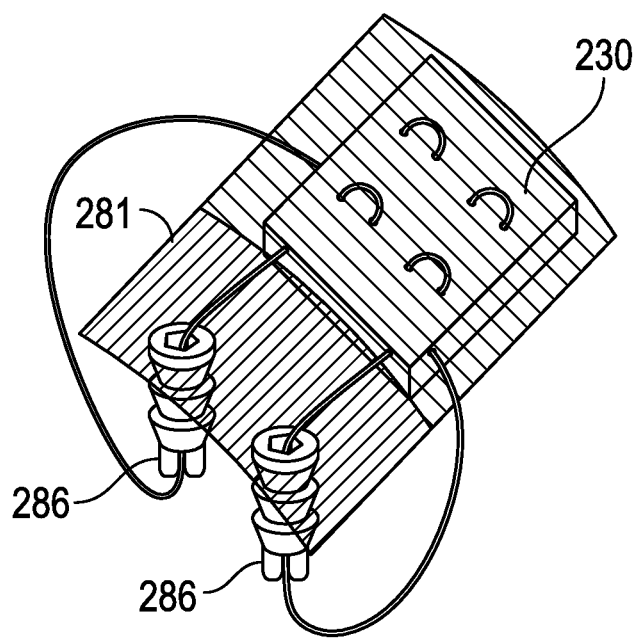
FIG. 13C schematically illustrates one exemplary method of fixation of a graft to bone.
Figure 13D:
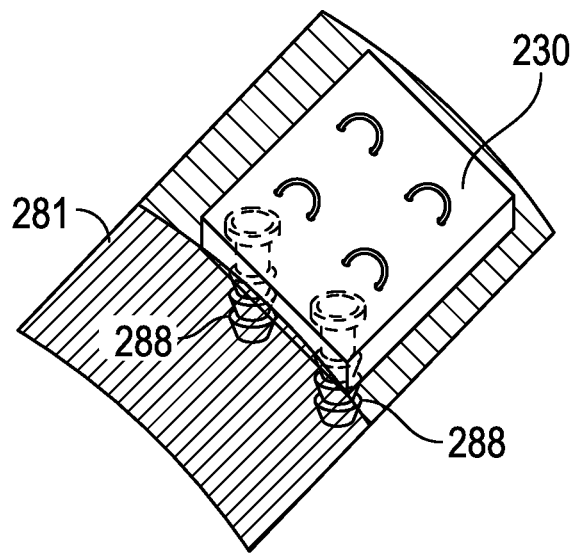
FIG. 13D schematically illustrates one exemplary method of fixation of a graft to bone.

Alternatively, as shown in FIGS. 13C and 13D, the graft 230 could be fixated directly to bone 281 without the use of sutures. As shown in FIG. 13C, the graft 230 could be loaded directly to one or more bone anchors 286 fixated to the bone 281. As shown in FIG. 13D, the graft 230 could be fixated to the bone 281 with one or more headed bone anchors 288.

Figure 14:
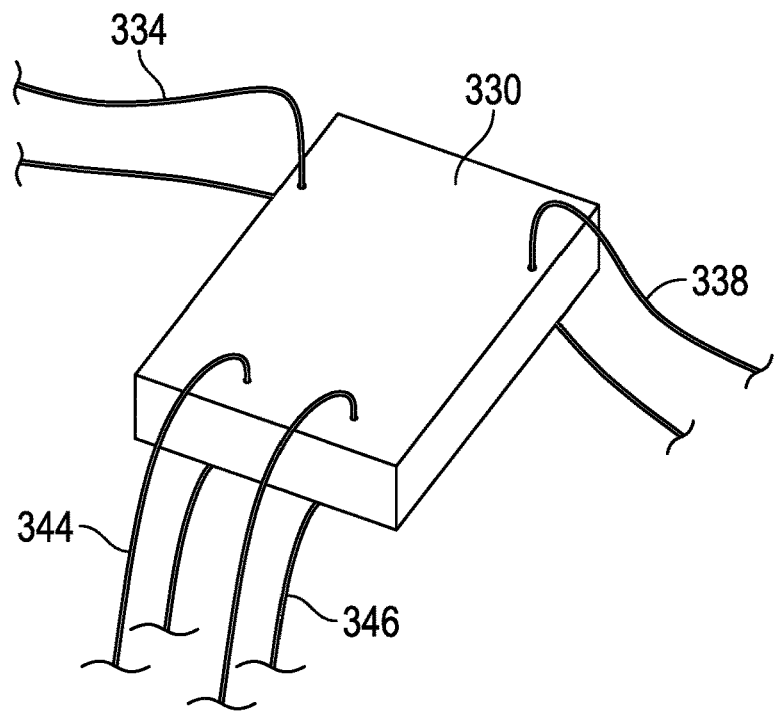
FIG. 14 schematically illustrates another technique for passing sutures through a graft.
Figure 15A:
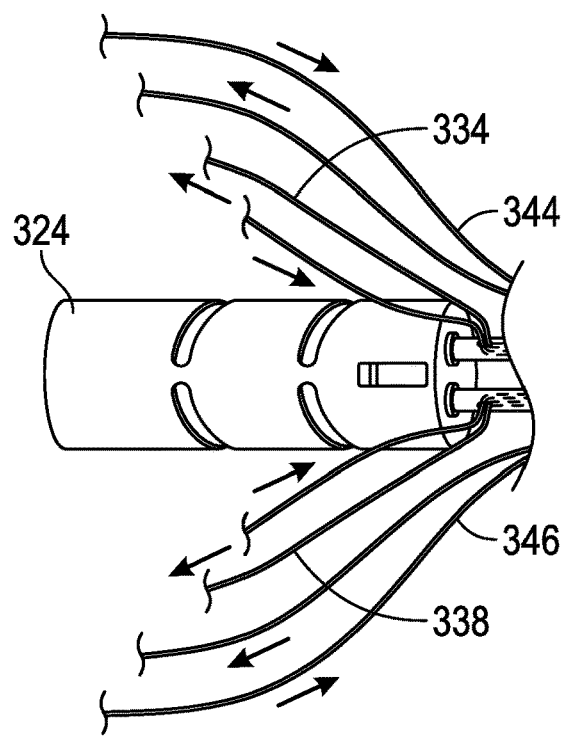
FIG. 15A schematically illustrates another technique of uncleating and removing sutures from a surgical tool for the graft shown in FIG. 14 during an exemplary graft augmentation technique.
Figure 15B:
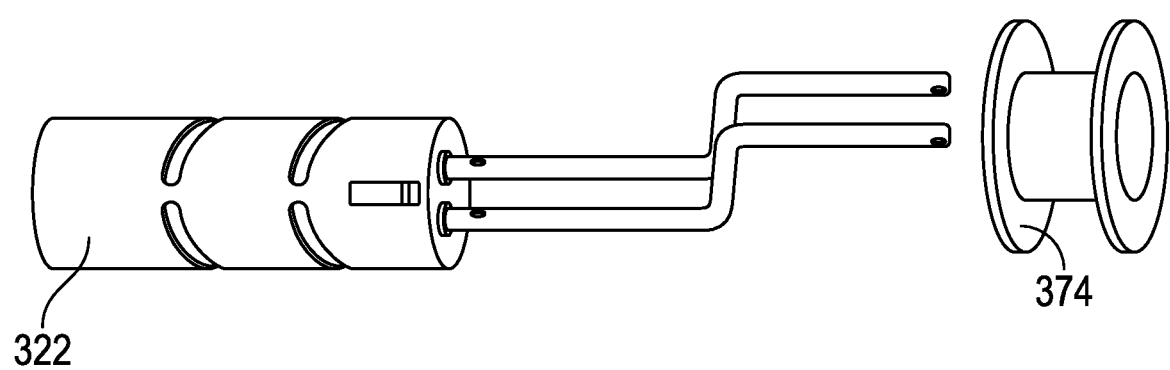
FIG. 15B schematically illustrates the removal of the surgical tool of FIGS. 14-15A from the joint space during an exemplary graft augmentation technique.

FIGS. 14-15B illustrate another exemplary graft augmentation technique 300. Referring first to FIG. 14, a surgeon may begin the graft augmentation technique 300 by preparing a graft 330 and passing a plurality of sutures 334, 338, 344, 346 through the graft 330. The technique 300 is similar to the technique 200 described above except that the sutures 344 and 346 are attached to the graft 230 with a U-shaped attachment, such that each of sutures 334, 338, 344, 346 may be removed from the graft 330 by pulling on one of their respective free ends.

The graft 330 may next be loaded onto the surgical tool 322, introduced to a joint space, and fixated to tissue in a similar manner as described with regard to the technique 200 and shown at FIGS. 7-11.

As shown in FIGS. 15A and 15B, once the graft 330 is secured to the soft tissue 376 (not shown), the surgical tool 322 is prepared to be removed. As shown in FIG. 15A, the sutures 334, 338, 344, 346 may be uncleated from the handle 324. The surgeon may then pull on a free end of each of the sutures 334, 338, 344, 346 to remove the sutures 334, 338, 344, 346 from the graft 230. As shown in FIG. 15B, the surgical tool 322 may then be moved to the folded position and removed from the joint space, such as through a cannula 374. In some embodiments, no further fixation to the bone may be needed in this technique.

The exemplary surgical tools 22/122/222/322 of this disclosure may be utilized in various graft augmentation techniques. These techniques may include superior capsular reconstruction, in some embodiments. In other embodiments, the exemplary surgical tools 22/122/222/322 may be utilized in any technique where a graft may be positioned against bone.

Although the different embodiments are illustrated as having specific components, the embodiments of this disclosure are not limited to those particular combinations. It is possible to use some of the components or features from any of the embodiments in combination with features or components from any of the other embodiments.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:
1. A method, comprising:
passing a first suture through a graft;
routing the first suture through a first arm of a surgical tool;

tensioning and cleating the first suture within a channel formed in an outer surface of a handle of the surgical tool;
passing a second suture through the graft;
routing the second suture through a second arm of the surgical tool;
tensioning and cleating the second suture within a second channel formed in the outer surface;
passing a third suture through the graft;
tensioning and cleating the third suture within a third channel formed in the outer surface;
folding the graft with the surgical tool;
inserting the folded graft through a cannula or an open incision;
unfolding the graft over a soft tissue;
securing the graft to the soft tissue with at least one fastener; after securing the graft, uncleating the first, second, and third sutures;
anchoring a lateral side of the graft to bone using the third suture; and
removing the first suture and the second suture from the graft after securing the graft to the soft tissue.

2. The method as recited in claim 1, wherein the securing step includes inserting the at least one fastener through the graft and through the soft tissue.

3. The method as recited in claim 2, wherein the at least one fastener includes first and second barbs connected by a bridge, and the first and second barbs pierce through the soft tissue and the bridge rests over the graft to secure it in place.

4. The method as recited in claim 1, wherein the first and second sutures are passed through the graft using U-shaped attachments, and the first and second sutures are removed by pulling the free ends of the first and second sutures.

5. The method as recited in claim 1,
routing the first suture through a first lumen of the first arm;
routing the second suture through a second lumen of the second arm;
wherein the third suture is cleated within the third channel and a fourth suture is cleated within a fourth channel without passing either of the third suture or the fourth suture through the first lumen or the second lumen.

6. The method as recited in claim 1, wherein the first arm includes an offset configuration.

7. The method as recited in claim 1, wherein the step of unfolding includes moving the surgical tool from a folded to a spread position.

8. The method as recited in claim 1, wherein the step of unfolding includes rotating the first arm relative to the handle.

* * * * *